United States Patent [19]

Lefkowith

[11] Patent Number: 5,238,813
[45] Date of Patent: Aug. 24, 1993

[54] DIAGNOSTIC METHOD FOR NEPHRITIS

[75] Inventor: James B. Lefkowith, St. Louis, Mo.

[73] Assignee: Washington University, St. Louis, Mo.

[21] Appl. No.: 896,851

[22] Filed: Jun. 12, 1992

Related U.S. Application Data

[63] Continuation of Ser. No. 629,298, Dec. 18, 1990, abandoned.

[51] Int. Cl.$^5$ .................. G01N 33/552; G01N 33/564
[52] U.S. Cl. .................... 435/7.21; 435/7.95; 435/962; 436/506; 436/527
[58] Field of Search .............. 435/7.92, 28, 7.95, 435/7.21, 962; 436/507, 506, 518, 527

[56] References Cited

U.S. PATENT DOCUMENTS

| | | | |
|---|---|---|---|
| 4,487,830 | 12/1984 | Coates et al. | 435/7 |
| 4,493,815 | 1/1985 | Fernwood et al. | 411/101 |
| 4,839,298 | 6/1989 | Kay et al. | 436/175 |

OTHER PUBLICATIONS

Harlow and Lane: *Antibodies A Laboratory Manual* (1988) pp. 402, 404, 496, 497.
Schumacher, Primer on Rheumatic Diseases, Published by Arthritis Foundation 96–110 (1988).
Lefkowith & Schreiner, J. Clin. Invest. 80, 947–956 (1987). October.
Munns & Freeman, Biochemistry 28, 10048–10054 (1989).
Kelley et al., Textbook on Rheumatology, W. B. Saunders Co. 1985, pp. 690–704.
Mannik et al., Systemic Lupus Erythmatasus, R. G. Lahita ed. John Wiley & Sons, N.Y. N.Y. (1987), pp. 333–351.
Tijssen, Practice & Theory of Enzyme Immunoassays, vol. 15, Elsevier, N.Y., N.Y. (1985), p. 476.

*Primary Examiner*—David Saunders
*Attorney, Agent, or Firm*—Scott J. Meyer

[57] ABSTRACT

A diagnostic method is disclosed for determining the presence of renal disease or nephritis in association with systemic lupus erythematosus which comprises assaying for anti-glomerular binding reactivity in sera using a solid phase enzyme-linked immunoassay.

1 Claim, 10 Drawing Sheets no 1°, no 2° no 1°

1:10

1:100

1:1,000

1:10,000

NRS   αGBM

Balb/c        MRL
              24wk

| PATIENT NO. | ANTI-GLOMERULAR REACTIVITY | ANTI-deDNA (O.D.) | CLINICAL STATUS |
|---|---|---|---|
| 0 | | 0.00 | NORMAL CONTROL |
| 3 | ● ● | 0.00 | FLARE PROTEINURIA (1.4g) CrCl 55 |
| 7 | ● ● | 0.31 | FLARE PROTEINURIA (0.6g) CrCl 81 |
| 14 | ● ● | 0.17 | STABLE PROTEINURIA (3.3g) CrCl 144 |
| 12 | | 0.16 | FLARE PROTEINURIA (tr) |
| 8 | ● ● | 1.5 | FLARE PROTEINURIA (0.6g) CrCl 116 BX:MESANGIOPATHIC |

FIG. 8

DIAGNOSTIC METHOD FOR NEPHRITIS

This is a continuation of application Ser. No. 07/629,298, filed Dec. 18, 1990 and now abandoned.

BACKGROUND OF THE INVENTION

This invention relates to a medical diagnostic method and, more particularly, to an in vitro diagnostic method for renal disease or nephritis in association with systemic lupus erythematosus.

Systemic lupus erythematosus (SLE) is a rheumatic disease; it is a chronic inflammatory disease that apparently results from an immunoregulatory disturbance caused by various factors. The lupus erythematosus cell is believed to result from an antinuclear antibody whereby SLE is characterized as an autoimmune systemic disease. The systemic nature of the disease is evident by various clinical manifestations, including renal involvement in SLE. The renal involvement is usually glomerular.

Various methods have been described heretofore for detecting renal disease in SLE. Thus, kidney biopsies have been widely used to determine renal involvement in SLE. Immunofluorescence is a principal technique used in identifying the immunopathogenesis of renal disease.

The presence of antinuclear antibodies (ANAs) is a diagnostic hallmark of SLE since ANAs appear in nearly all patients with SLE. The fluorescent-ANA test is one of the most widely used and accepted tests for the detection of circulatory ANAs.

Antibodies to DNA have been useful in specific tests in rheumatology. On the one hand, high-affinity antibodies reacting with double-stranded DNA (dsDNA) are virtually unique to patients with SLE and only rarely found in other conditions. On the other hand, low-affinity antibodies that react with denatured or single-stranded DNA (ssDNA) occur in a wide variety of other rheumatic diseases.

BRIEF DESCRIPTION OF THE INVENTION

In accordance with the present invention a diagnostic method is provided for determining the presence of renal disease or nephritis in association with systemic lupus erythematosus (SLE) in a warm blooded mammal. The method comprises assaying for anti-glomerular binding reactivity in sera of the mammal using a solid phase enzyme-linked immunoassay.

In a preferred embodiment of the invention, enzyme digested murine glomeruli retained in a solid-phase carrier are placed in a plurality of the wells of a plastic microplate or similar such multiwell test apparatus and treated with a dilute buffered solution of goat serum to serve as a blocking agent. The test mammalian sera are placed in serial dilutions in buffered solution of goat serum, added to the wells and allowed to react for a predetermined period of time. A detecting reagent of goat anti-mouse immunoglobulin or goat anti-human immunoglobulin linked to horseradish peroxidase in dilute buffered solution of goat serum is then added to the wells and allowed to react for a substantially similar period of time. The thus treated glomeruli are then inoculated with a developing reagent of chloronaphthol in buffered solution. Positive wells appear as blue-black dots whereas negative wells are yellowish dots.

The buffering agents used in the diagnostic method are preferably isotonic and selected to provide a physiologically acceptable pH of about 7 to 8 for the reagent solutions. Phosphate-buffered saline (PBS) and tris(hydroxymethyl)aminomethane are representative examples of suitable buffers.

For the blocking agent, any source of serum can be used such as, for example, goat, equine or bovine sera. However, the blocking serum selected should not be of the same species as the test serum; i.e., human blocking serum should not be used for the assay of human serum, nor should mouse blocking serum be used for the assay of murine serum. The assay generally can be run with a dilution of serum of from about 5% to 20%.

The detecting reagent can be any reagent capable of detecting human or murine immunoglobulin which is suitably labelled. Illustrative examples are: 1) an anti-mouse or anti-human immunoglobulin (poly- or monoclonal) from any mammalian species, but preferably from goat source; 2) anti-immunoglobulin reagents such as Protein A or G. Suitable labels can be, e.g., enzymes, radioactivity, fluorochromes, colloidal gold and biotin. Representative enzymes for the labelling are peroxidase and galactosidase. A preferred radioactive label is $^{125}I$. For biotin, a subsequent step in which the glomeruli are incubated with streptavidin or avidin (which bind to biotin) linked to an enzyme, fluorochrome, colloidal gold or radioactivity is generally necessary.

The developing reagent can be any reagent capable of detecting the presence of bound detecting antibody. The developing reagent will depend on the nature of the label used. For enzymes, any substrate which produces an insoluble colored product, e.g. chloronaphthol, can be used. Substrates which produce light (chemiluminescence) can also be used. For colloidal gold, a gold stain is used as the developing reagent. Biotin, as indicated above, requires an extra incubation step with labelled streptavidin or avidin. For radioactivity or fluorochromes, no developing reagent is necessary inasmuch as these labels can be directly detected.

The assay is preferably carried out with a dot-blot apparatus and glass fiber filter. Any filtration device is suitable for the assay and any filter with a pore size of less than 70µ can be used. The commercially available Bio-Dot ® microfiltration apparatus which consists of a 96 well vacuum filtration unit that is also described in U.S. Pat. No. 4,493,815, is illustrative of useful apparatus.

Reaction times for the reagent reactions can be any predetermined time sufficient for detection. Generally, reaction times of from about 30–60 minutes are suitable.

Although specific materials and apparatus for use in the diagnostic method of the invention are described herein, it will be appreciated that the invention is not limited to use of these specific materials and apparatus which are illustrative and not limitative of the invention.

The component reagents for use in the diagnostic method of the invention can be assembled in the form of a diagnostic kit for convenient use by clinical laboratories, hospital laboratories, doctors' offices and the like. For example, the diagnostic kit can comprise a glomeruli substrate, a detecting antibody and a detecting (developing) reagent. Illustratively, the substrate can be a glomerular preparation which is fresh material, suspended in buffer and the like; the detecting antibody can be goat anti-human immunoglobulin labelled with horseradish peroxidase, which can be in buffer or prepared to be reconstituted in buffer by the user; and the detecting (developing) reagent can be chloronaphthol prepared to be reconstituted by the user. The diagnostic kit can optionally include buffer, with and without serum, either in ready to use form or prepared to be reconstituted prior to use; hydrogen peroxide; and methanol (for preparation of the chloronaphthol reagent). The kit can include any of the alternative reagents such as described herein for use in the diagnostic method of the invention.

DETAILED DESCRIPTION OF THE INVENTION

While the specification concludes with claims particularly pointing out and distinctly claiming the subject matter regarded as forming the present invention, it is believed that the invention will be better understood from the following description taken in conjunction with the accompanying drawings in which, briefly:

FIG. 1 (FIG. 1A and FIG. 1B) shows the dot-blot results of inoculating glomeruli with various dilutions of rabbit anti-rat glomerular basement membrane antibody ($\alpha$GBM) in FIG. 1A and FIG. 1B or normal rabbit serum (NRS) in FIG. 1A in an enzyme-linked immunoassay.

FIG. 2 (FIG. 2A and FIG. 2B) shows the results of an assay as in FIG. 1 in which various dilutions of sera from MRL lpr mice and non-autoimmune mice (Balb/c) were tested for anti-glomerular reactivity at 24 weeks (wks) in the panel of FIG. 2A and from MRL at various weeks (6-36 wks) and from Balb/c at 24 weeks in the panel of FIG. 2B.

In a conventional enzyme-linked immunosorbent assay (ELISA), an antigen or antibody is linked to an insoluble carrier surface. The thus sensitized carrier surface captures the corresponding antibody or antigen from the test solution (e.g., serum). An enzyme-labelled antiglobulin attaches to the antigen or antibody complex, which is detected by the enzyme label changing the color of an added substrate. The optical density of the final color is directly proportional to the amount of unknown antibody or antigen in the original test solution. See, e.g., Engvall and Perlmann, *Immunochemistry* 8, 871-874 (1971); *J. Immunol.* 109, 129-135 (1972).

In a typical ELISA procedure, horseradish peroxidase is used as the labeling enzyme and o-phenylenediamine is used as the peroxidase substrate. The reactions are conveniently carried out in plastic microplate wells in which the colorimetric end-point is determined by a spectrophotometric reading at, e.g., 492 nm. The optical density can be plotted against concentration of the known antibody linked to the carrier and the concentration of the unknown calculated from a standard curve.

Although various principles of the foregoing conventional ELISA technology are employed in the diagnostic method of the invention, the differences and advances over this art will be seen from the following summary of the anti glomuler reactivity in murine and human lupus sera in conjunction with the detailed illustrative examples.

ANTI GLOMERULAR REACTIVITY IN MURINE AND HUMAN LUPUS SERA

Although the immune complex hypothesis has important explanatory power in systemic lupus erythematosus (SLE), the exact pathogenesis of renal inflammation in SLE is not entirely clear. It has been argued the immune complexes, cross-reactive anti-DNA antibodies, or planted antigens in the glomerulus (such as DNA) may mediate the renal disease. Additionally, there is a paucity of non-invasive means to assess renal disease in SLE. Using both fluorescence labelling and a solid phase enzyme-linked immunoassay, substantial anti-glomerular binding activity was detected in the serum of MRL lpr mice by non-invasive means in illustrative examples hereinbelow. The pattern of fluorescence did not correspond to any simple glomerular structure and was distinct from anti-basement membrane staining. Anti-glomerular reactivity was apparent at 12 weeks of age and increased in parallel with the development of nephritis in this strain. Binding activity was reduced by preadsorption to glomeruli but not by preadsorption to glomerular basement membrane or non-renal tissue (macrophage, platelets, erythrocytes, splenic mononuclear cells or hepatocytes). Preadsorption of serum with DNA-agarose was ineffective in removing the anti-glomerular reactivity although >90% of the anti-DNA binding activity was removed. Pre-exposure of serum to DNAse removed much, though not all, of the glomerular binding activity. Binding activity in murine lupus serum was neither enhanced nor inhibited with the addition of ss or ds DNA. Heat-aggregated immunoglobulin did not block the binding activity of lupus serum. Binding activity was also present in sera from patients with SLE (16/20 patients). Binding activity correlated with clinical disease as determined by the anti-DNA response. The most markedly positive tests were all in patients with evidence of nephritis. Thus, glomerular binding activity is present within the serum of MRL lpr mice and patients with SLE. This binding activity appears to be specific to glomerular cells, to involve the presence of intact DNA, to correlate with renal disease, and may be of pathogenic significance. Assaying for anti-glomerular reactivity as disclosed herein provides an alternative and novel means to non-invasively assess renal disease in SLE.

The following detailed examples will further illustrate the diagnostic method of the invention although it will be understood that the invention is not limited to these specific examples.

EXAMPLE 1

A general anti-glomerular assay was carried out stepwise according to the following protocol. In this assay, various described materials were obtained from the following sources.

| Material | Source |
| --- | --- |
| Dot-blot apparatus | Bio-Rad, Richmond, CA, #170-6545 |
| Glass fiber filter | Skatron, Sterling, VA, #11731 |
| Goat serum | Gibco, Grand Island, NY |
| Peroxidase-labelled antibody (for detection) | for human: Sigma, St. Louis, MO, A8667 |
| | for mouse: Bio-Rad, Richmond, CA, #170-6516 |
| Chloronaphthol | Bio-Rad, Richmond, CA, #170-6534 |

ANTI-GLOMERULAR ASSAY PROTOCOL

1. Glomeruli are isolated from rats and digested with collagenase/DNAse type I using a conventional, published protocol by Lefkowith and Schreiner, *J. Clin. Invest.* 80, 947-956, (1987).
2. Prepared glomeruli are then fixed to a glass fiber filter as the solid phase using a 96 well dot-blot apparatus. Approximately 500 glomeruli are added to each well in phosphate-buffered saline (PBS).
3. A blocking solution of 10% goat serum in PBS (PBSS) is applied to the glomeruli for 30 min.
4. The glomeruli are washed three times with PBS by filtration.
5. Mouse or human serum in varying dilutions in PBSS is then added to the wells containing the glomeruli for 1 hr at room temperature.
6. The glomeruli are again washed three times with PBS by filtration.
7. A detection reagent (either goat anti-mouse immunoglobulin or goat anti-human immunoglobulin, each linked to horseradish peroxidase) diluted in PBSS is added to the wells containing the glomeruli for 1 hr at room temperature.
8. The glomeruli are washed twice with PBS and twice with Tris-buffered saline (TBS) by filtration.
9. The glass fiber filter is then removed from the dot-blot apparatus and incubated in a developing reagent (4-chloro-1-naphthol in TBS) for 30 minutes. Positive wells appear as blue-black dots whereas negative wells are yellowish dots.

The aforesaid assay was employed in Examples 2-9 in which the results are also set forth in FIGS. 1-8, respectively.

EXAMPLE 2

Figure 1A:
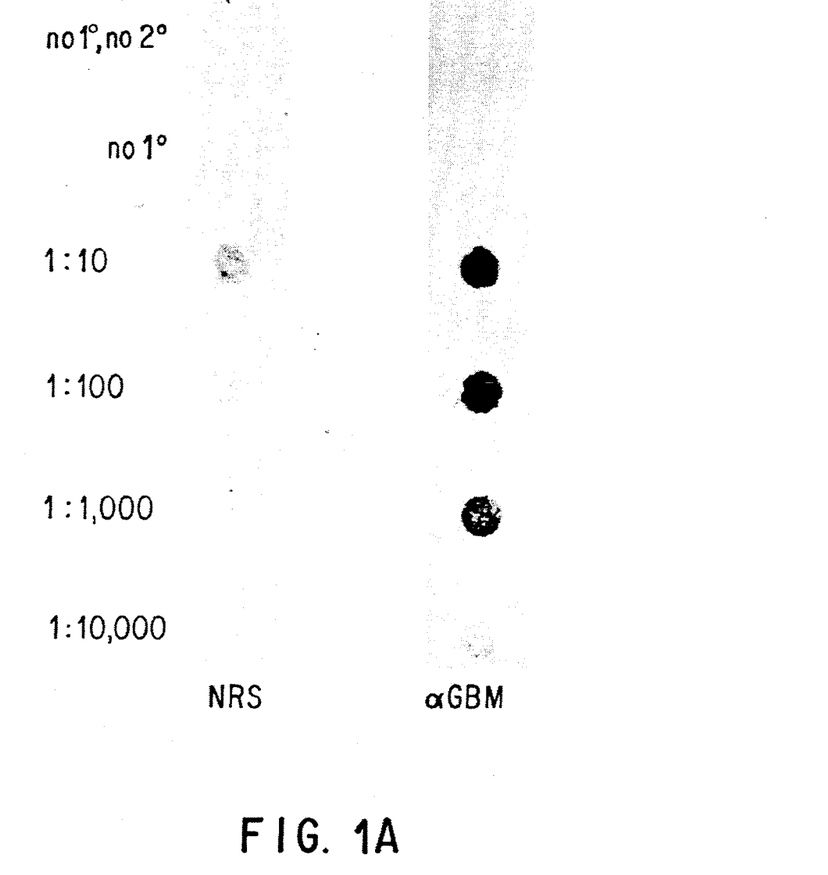
Figure 1B:
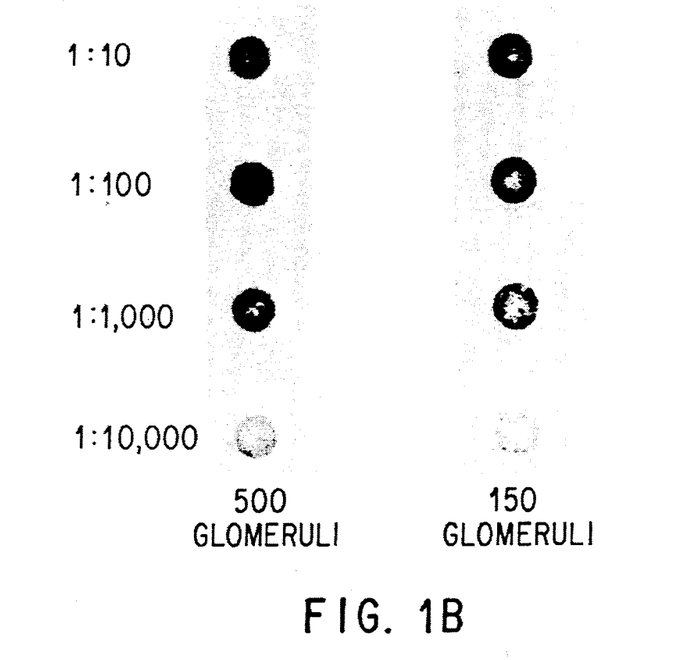

This example, as illustrated in FIG. 1, shows the validation of the assay using an experimentally derived anti-glomerular basement membrane antibody. Using the aforementioned protocol of Example 1, glomeruli were incubated with varying dilutions (indicated on the left in panels A and B of FIG. 1) of rabbit anti-rat glomerular basement membrane antibody ($\alpha$GBM) or normal rabbit serum (NRS). As shown in the panel of FIG. 1A, the anti-basement membrane antibody binds to the glomeruli (as demonstrated by the dark dots) whereas the normal serum does not. The panel of FIG. 1B documents that the signal strength is proportional to the number of glomeruli placed in the well initially.

EXAMPLE 3

Figure 2A:
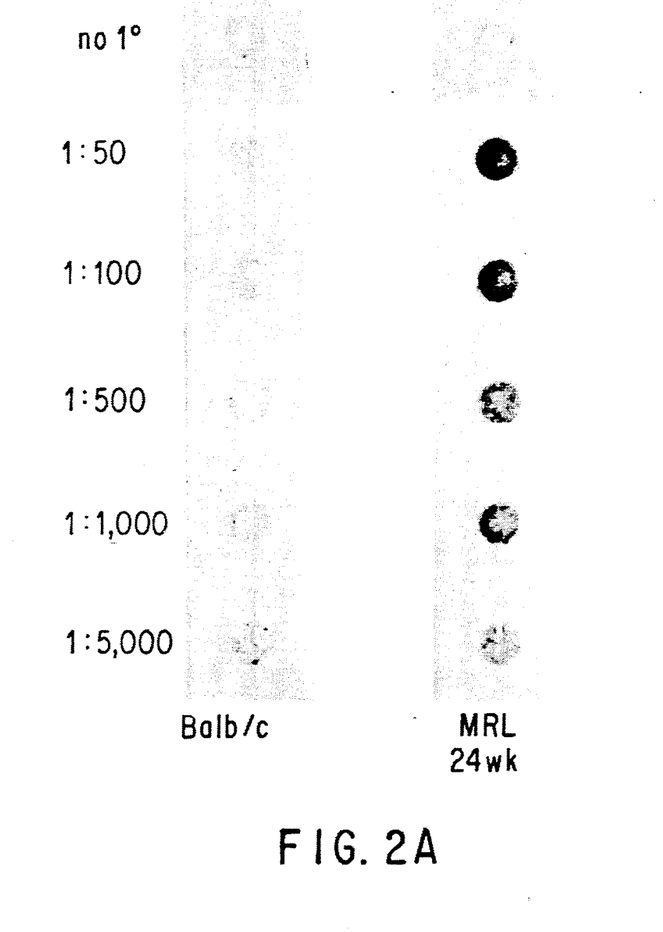
Figure 2B:
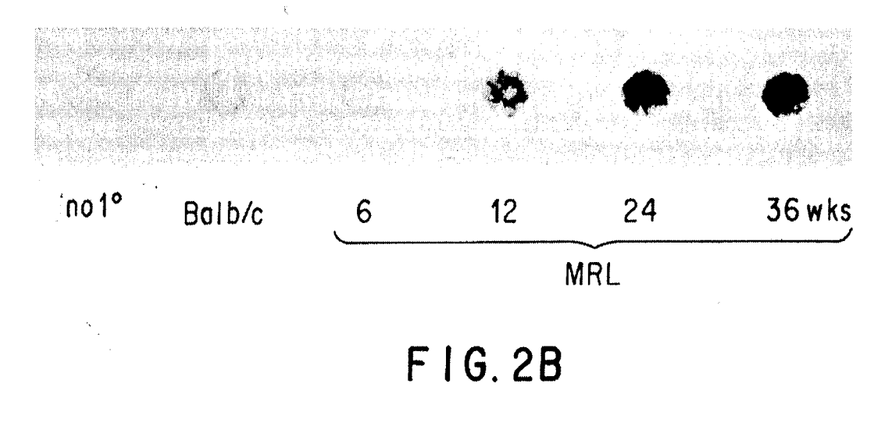

This example, as illustrated in FIG. 2, gives a demonstration of glomerular binding activity in the MRL lpr mouse and its relationship to glomerulonephritis. Using the above assay system, pools of serum from MRL lpr mice (a standard animal model of SLE) were tested for anti-glomerular reactivity. As shown in the panel of FIG. 2A, anti-glomerular reactivity is present in high titer (>1:5000) in MRL mice but not in non-autoimmune mice (Balb/c). Anti-glomerular reactivity increases with age, as demonstrated in the panel of FIG. 2B, paralleling the development of nephritis in this strain.

EXAMPLE 4

Figure 3:
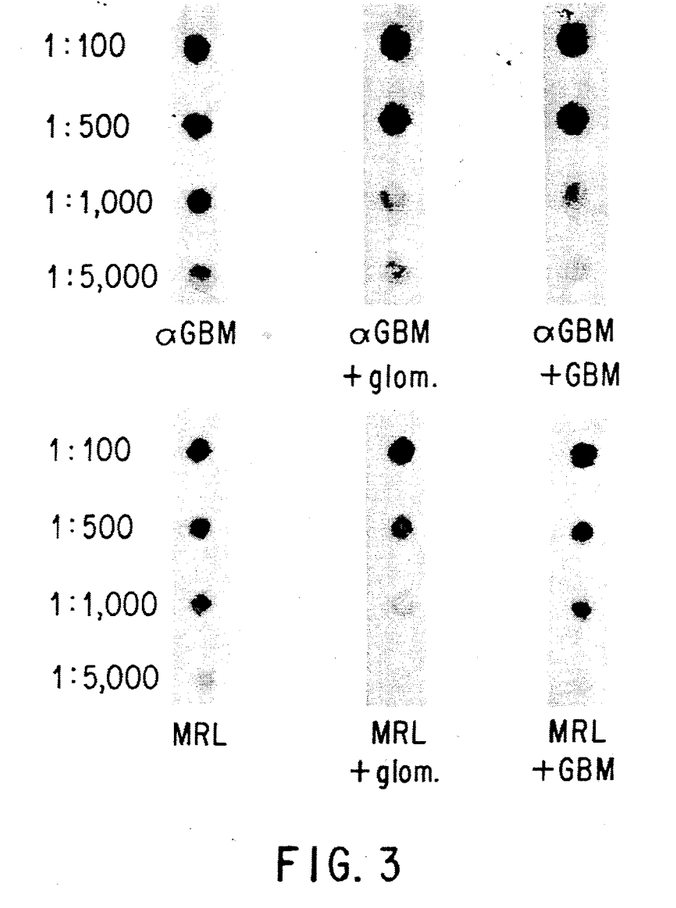
FIG. 3 shows the results of an assay as in FIG. 2 in which the MRL lpr serum was preincubated with either whole glomeruli (+glom.) or purified basement membrane (+GBM) and compared with control in which anti-GBM antibody ($\alpha$GBM) was also preincubated with both glomeruli and GBM.

This example, as illustrated in FIG. 3, shows the target of anti-glomerular reactivity in MRL serum. MRL lpr serum (MRL) was preincubated with either whole glomeruli or purified basement membrane (GBM). As shown in FIG. 3, only preincubation with whole glomeruli (not GBM) reduces the titer of the serum. As a control, anti-GBM antibody was also preincubated with both glomeruli and GBM. Preincubation with both reduces the reactivity of the anti-GBM antibody. Additional tests demonstrated that preincubation with other tissues (namely erythrocytes, platelets, macrophages, splenic mononuclear cells and hepatocytes) does not reduce the activity of the MRL serum.

EXAMPLE 5

Figure 4:
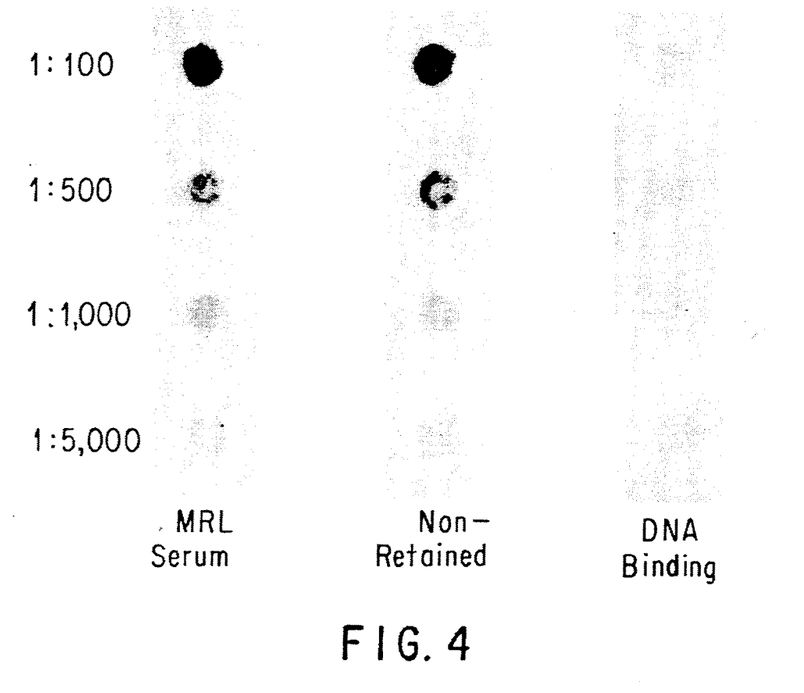
FIG. 4 shows the results of an assay as in FIG. 2 in which the MRL lpr serum was preadsorbed with DNA-agarose and separated into DNA Binding or non-DNA Binding (Non-Retained) fractions.

This example, as illustrated in FIG. 4, shows that anti-glomerular reactivity is distinct from anti-DNA reactivity. MRL lpr serum was separated into DNA or non-DNA binding (non-retained) fractions using DNA linked to agarose. The glomerular binding activity of the serum was wholly in the non-retained or non-DNA binding fraction. This demonstrates that the anti-glomerular reactivity is different from anti-DNA reactivity.

EXAMPLE 6

Figure 5:
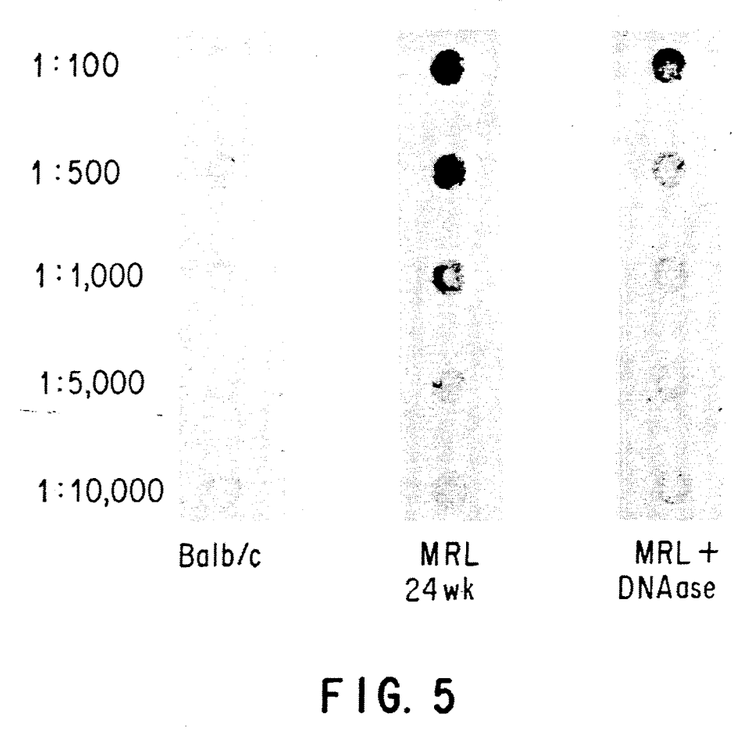
FIG. 5 shows the results of an assay as in FIG. 2 in which the MRL lpr serum was pre-exposed to DNAase (MRL+DNAase) or non-exposed (MRL 24 wk).

This example, as illustrated in FIG. 5, shows that anti-glomerular reactivity is dependent in part on the presence of intact DNA. MRL lpr serum was subjected to DNAse treatment to digest and remove DNA to assess whether DNA was an important factor in anti-glomerular reactivity. As shown in FIG. 5, DNAase treatment removes much, but not all of the anti-glomerular reactivity, suggesting that intact DNA is important in the binding reaction.

EXAMPLE 7

Figure 6:
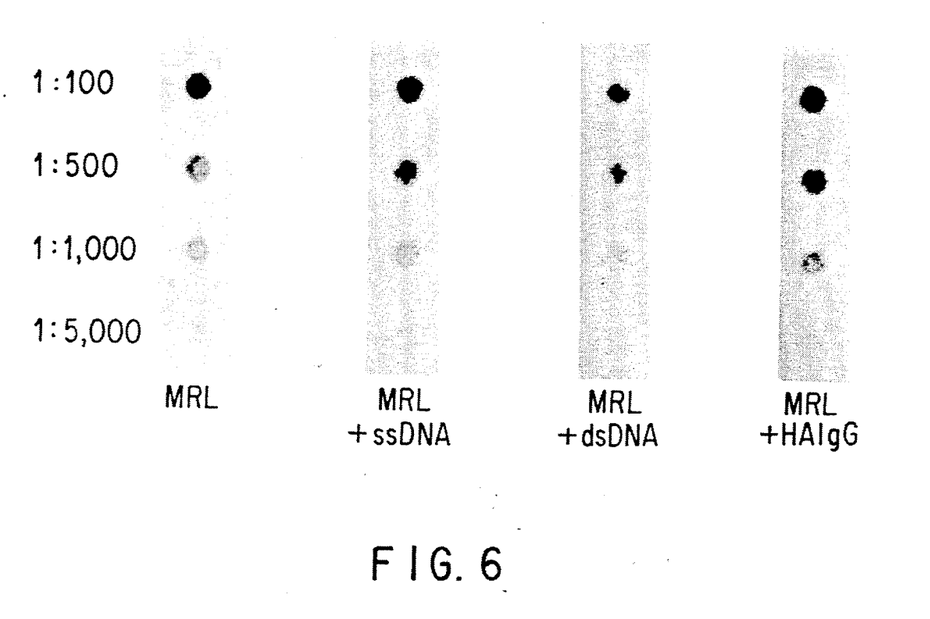
FIG. 6 shows the results of an assay as in FIG. 2 in which the MRL lpr serum was pre-exposed to either single-stranded (ss) or double-stranded (ds) DNA or heat aggregated immunoglobulin (HAIgG).

This example, as illustrated in FIG. 6, demonstrates the effect of exogenous DNA or heat-aggregated IgG (HAIgG) on anti-glomerular reactivity. Either exogenous single-stranded (ss) or double-stranded (ds) DNA or HAIgG was added to MRL lpr serum to assess the effect on the glomerular binding activity. As shown in FIG. 6, none of these manipulations affect glomerular binding activity. This result implies that the binding activity in MRL serum is not binding through either DNA receptors or Fc receptors (i.e. immunoglobulin receptors).

EXAMPLE 8

Figure 7:
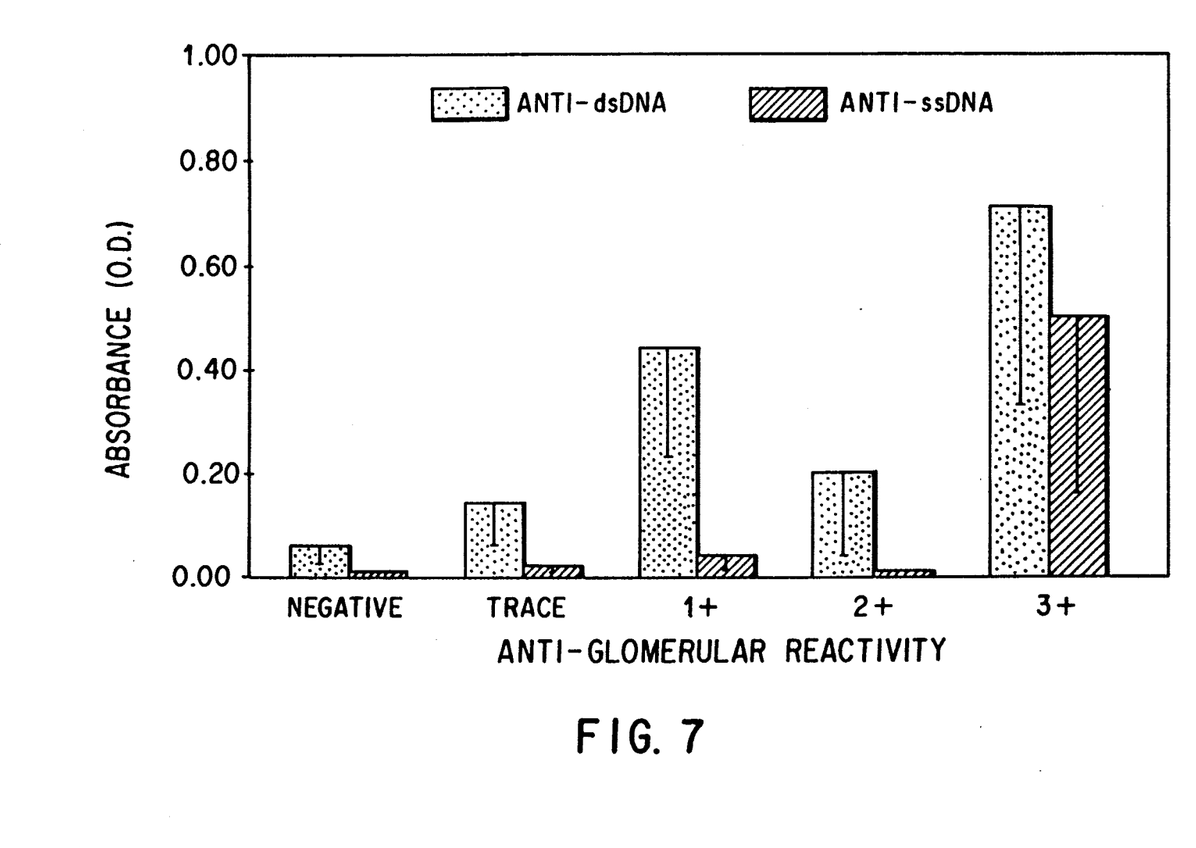
FIG. 7 is a bar graph which shows the results of an assay in which serum from 20 patients with SLE were tested for anti-glomerular reactivity as in FIG. 2 and demonstrates the correlation of the reactivity with the disease as measured by $\alpha$DNA ELISA.

This example, as illustrated in FIG. 7, indicates that anti-glomerular reactivity in human SLE is correlated with disease. Anti-glomerular reactivity was determined with the aforementioned system in 20 patients with SLE. Positive tests were observed in 16 of 20 patients. Anti-glomerular reactivity was correlated with disease activity using the anti-DNA response (a standard laboratory measure of disease activity) as measured by αDNA ELISA [Munns and Freeman, *Biochemistry* 28, 10048 (1989)]. As shown in FIG. 7, both tests are correlated (i.e. a positive anti-glomerular reactivity test is associated with a higher titer of anti-DNA antibodies).

EXAMPLE 9

Figure 8:
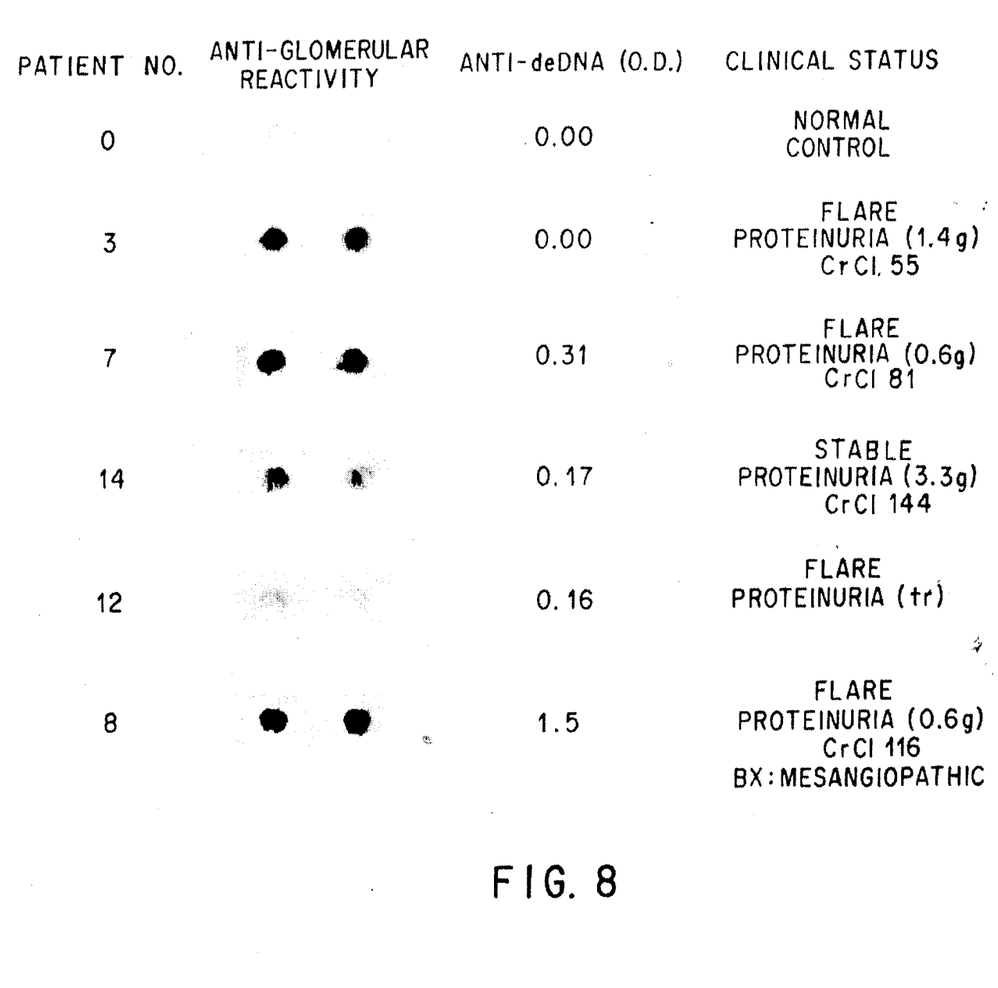
FIG. 8 shows the anti-glomerular reactivity of 5 selected patients from the group of 20 shown in FIG. 7.

This example, illustrated in FIG. 8, shows the anti-glomerular reactivity in selected patients with SLE. The clinical records of the four patients from Example 8 with the most positive anti-glomerular reactivity tests (3+) were examined. All four patients had clinical evidence of renal disease. Three of these patients were considered to be having a disease flare-up. Only 1 patient had been identified as being at risk for renal disease in the clinic using the anti-DNA response in the Farr assay (Textbook of Rheumatology, Kelley et al., eds., W. B. Saunders Company, 1985, pp. 690-704). This patient also had a marked increase in anti-DNA antibodies in the ELISA assay. The other three patients had low-level positive or negative anti-DNA tests. The records of one patient from Example 8 with a 1+ positive anti-glomerular test was also examined. This patient was having a disease flare-up but had little renal disease that was clinically apparent. Thus a marked positive anti-glomerular reactivity test as disclosed herein can identify patients with lupus nephritis and is superior to the anti-DNA test.

Various other examples will be apparent to the person skilled in the art after reading the present disclosure without departing from the spirit and scope of the invention, and it is intended that all such other examples be included within the scope of the appended claims.

What is claimed is:

1. An in vitro diagnostic method for non-invasively determining anti-glomerular binding reactivity as distinguished from anti-DNA reactivity in the sera of a mouse or human host affected with SLE comprising:
   a) digesting rat glomeruli with a mixture of collagenase and DNase type I enzymes,
   b) binding said enzyme-digested glomeruli to a glass fiber carrier in a plurality of incubation wells,
   c) incubating said enzyme-digested and carrier-bound glomeruli with a dilute buffered solution of from about 5% to 20% by weight blocking serum of a xenogeneic mammal in said wells,
   d) reacting the thus-incubated glomeruli with serial dilutions of the sera of said mouse or human host for a predetermined period of time in said wells,
   e) adding to said wells a detecting reagent of goat anti-mouse immunoglobulin or goat anti-human immunoglobulin linked to horseradish peroxidase,
   f) allowing said detecting reagent to react for a predetermined period of time substantially similar to the time in step d,
   g) adding to said wells a developing reagent of chloronaphthol,
   h) observing the resulting color formation in said wells in which blue-black color formation indicates a positive diagnostic result of anti-glomular binding reactivity and yellow color formation indicates a negative diagnostic result, and in which said steps c through g are carried out in physiologically acceptable buffer at pH of about 7 to 8.

* * * * *